US00PP18780P3

(12) United States Plant Patent

Zaiger et al.

(10) Patent No.: US PP18,780 P3

(45) Date of Patent: Apr. 29, 2008

(54) INTERSPECIFIC TREE

(50) Latin Name: **Interspecific *Prunus* species**
Varietal Denomination: Flavor Crisp

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 170 days.

(21) Appl. No.: 11/474,534

(22) Filed: Jun. 27, 2006

(65) Prior Publication Data

US 2007/0300335 P1 Dec. 27, 2007

(51) Int. Cl.
*A01H 5/00* (2006.01)

(52) U.S. Cl. ..... Plt./180

(58) Field of Classification Search ..... Plt./184
See application file for complete search history.

*Primary Examiner*—S. B. McCormick-Ewoldt

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, irrigation and fertilization. Its novelty consist of the following combination of desirable features:

1. The tree with a vigorous, upright growth habit.
2. Fruit that matures in the early season.
3. Relatively uniform size fruit throughout the tree.
4. Fruit with very good flavor and eating quality.
5. Fruit with good handling and shipping quality.

1 Drawing Sheet

Botanical classification: Interspecific *Prunus* species.

BACKGROUND OF THE VARIETY

FIELD OF THE INVENTION

In the field of plant genetics, we conduct an extensive, and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

The existing plum variety that is known to us, and mentioned herein, is 'Red Beaut' Plum (U.S. Plant Pat. No. 2,539).

ORIGIN OF THE VARIETY

The present new variety of interspecific tree [*Prunus salicina*×(*Prunus salicina*×*Prunus armeniaca*)] was originated by us in our experimental orchard located near Modesto, Calif. from seed of an open pollinated seedling selection of the proprietary interspecific seedling with the field identification number '45GH74'. The interspecific seedling (45GH74) originated from an open pollinated seedling, which was developed from the cross of a plum of unknown parentage and our proprietary plumcot (4G1180). The plumcot selection (4G1180) originated from an open pollinated selected seedling of 'Red Beaut' Plum (U.S. Plant Pat. No. 2,539), which was crossed with an apricot of unknown parentage. A large group of these open pollinated seedlings were planted and grown on their own root system. Under close and careful observation, one such seedling which is the present variety, exhibited desirable fruit characteristics and in 1994, was selected for asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of interspecific tree (Plum× Plumcot) is of large size, vigorous upright growth, and a productive and regular bearer of medium to large, yellow flesh fruit with very good flavor and eating quality. The fruit is further characterized by its firm flesh, being relatively uniform in size throughout the tree, having good handling and storage quality and maturing in the early season. In comparison to 'Red Beaut' Plum (U.S. Plant Pat. No. 2,539) the present variety has heavier production of fruit with skin that is bicolored red and yellow instead of red and is approximately 6 days later in maturity. In comparison to its maternal parent (45GH74) the skin of the fruit is bicolored instead of red, has yellow flesh instead of yellow-red flesh and matures approximately 12 days earlier.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, 7 years of age, its flowers, foliage and fruit, as based on observations of 7 year old specimens grown near Modesto, Calif., with color in accordance with Munsell Book of Color.

Tree

*Size.*—Large. Pruned to approximately 3 to 3.5 meters in height for economical harvesting of fruit. Average spread 3 meters, varies with different cultural practices.

*Vigor.*—Vigorous, growth of 1.5 to 2 meters the first growing season, varies with fertility, type of soil and climatic conditions.

*Form.*—Upright, usually pruned to vase shape.

*Branching habit.*—Upright, crotch angle approximately 35°, increases with heavy production.

*Productivity.*—Productive, thinning and spacing of fruit necessary for desirable market size fruit.

*Bearer.*—Regular. Adequate fruit set five consecutive years. No alternate bearing observed.

*Fertility.*—Self-sterile, pollinator required.

*Density.*—Medium dense. Usually pruned to vase shape to allow more sunlight to center of tree to improve fruit spur growth and fruit skin color.

*Hardiness.*—Hardy in all stone fruit growing areas of California. Winter chilling requirement approximately 500 hours at or below 45° F. Tree grown in USDA Hardiness Zone 9.

Trunk:

*Size.*—Large, stocky. Average circumference 63.5 cm measured at 28 cm above ground on a 7 year old tree.

*Texture.*—Medium shaggy, becomes rougher with age.

*Color.*—Varies from 10YR 2/2 to 2.5Y 6/2.

Branches:

*Size.*—Medium. Average circumference 19.3 cm measured at 1.2 meters above ground. Average crotch angle 35°, increases with heavy fruit production.

*Surface texture.*—New growth relatively smooth, mature growth moderately rough, increases with age.

*Lenticels.*—Average number 22 in a 25.8 square cm surface. Average length 3.9 mm. Average width 2.1 mm. Color varies from 7.5YR 6/8 to 7.5YR 5/8.

*Color.*—New growth varies from 5GY 4/6 to 5YR 3/4, where exposed to the sun. Old growth varies from 2.5YR 2/4 to 5YR 2/4, varies with age of growth.

Leaves:

*Size.*—Large. Average length 132.8 mm. Average width 65.1 mm.

*Form.*—Elliptic.

*Apex.*—Acuminate.

*Base.*—Cuneate.

*Margin.*—Doubly serrate.

*Thickness.*—Medium.

*Surface texture.*—Upper surface relatively smooth, slight indentations over midrib and leaf veins, glabrous. Lower surface relatively smooth except for small ridges created by midrib and pinnate venation, glabrous.

*Petiole.*—Average length 23.1 mm. Average width 1.9 mm. Longitudinally grooved. Color varies from 5GY 6/6 to 10R 3/4, varies with exposure to sunlight. Surface — glabrous.

*Glands.*—Type — globose. Size — medium. Average length 0.6 mm. Average diameter 0.4 mm. Number varies from 0 to 2, average number 1. Located primarily on base of leaf blade and upper portion of the petiole. Color varies from 2.5GY 4/4 to 5GY 5/6.

*Color.*—Upper surface varies from 2.5GY 3/4 to 5GY 3/4. Lower surface varies from 5GY 5/4 to 5GY 4.4. Midvein color varies from 10Y 7/4 to 2.5GY 7/4.

Flower buds:

*Size.*—Small to medium. Average length 11.9 mm. Average diameter 5.6 mm.

*Hardiness.*—Hardy in all stone fruit growing areas of California, with respect to California winters.

*Form.*—Conical, becoming elongated before opening.

*Pedicel.*—Surface — glabrous. Average length 9.1 mm. Average width 0.6 mm. Color — varies from 2.5GY 7/8 to 2.5GY 6/8.

*Color.*—N 9.5/ (white).

*Number of buds per spur.*—Average number 6, varies from 4 to 8. Varies with age of spur.

Flowers:

*Size.*—Medium. Average height 13.3 mm. Average diameter 23.3 mm.

*Petals.*—Number 5, alternatively arranged to sepals. Size — medium. Average length 13.1 mm. Average width 10.5 mm. Form — obovate. Margin — sinuate. Both surfaces glabrous. Color — N 9.5/ (white).

*Sepals.*—Number 5, alternately arranged to petals. Form — ovate, apex rounded. Margin — entire. Size — small. Average length 4.1 mm. Average width 2.8 mm. Both surfaces glabrous. Color — upper surface 2.5GY 6/10. Lower surface 2.5GY 5/8.

*Stamens.*—Average number per flower 33, varies from 30 to 35. Average filament length 8.5 mm. Filament color N 9.5/ (white). Anther color 2.5Y 8/14.

*Pollen.*—Self-sterile, pollinator required. Color — 2.5Y 7/12.

*Pistil.*—Normally 1. Surface glabrous. Average length 13.0 mm. Position of stigma — average of 2.1 mm above anthers. Color varies from 10Y 8.5/6 to 10Y 8/8.

*Fragrance.*—Slight aroma.

*Blooming period.*—Date of First Bloom Feb. 13, 2005. Date of Petal Fall Feb. 22, 2005, varies slightly with climatic conditions.

*Color.*—N 9.5/ (white).

*Number flowers per flower bud.*—Average number 2, varies from 1 to 3.

*Pedicel.*—Average length 12.2 mm. Average width 0.6 mm. Color varies from 2.5GY 7/8 to 2.5GY 6/10.

Fruit:

*Maturity when described.*—Firm ripe.

*Date of first picking.*—Jun. 6, 2005.

*Date of last picking.*—Jun. 12, 2005, varies slightly with climatic conditions.

*Size.*—Medium to large. Average diameter axially 54.9 mm. Average transversely in suture plane 62.7 mm. Average weight 119.8 grams, varies slightly with fertility of the soil, amount of thinning and climatic conditions.

*Form.*—Globose.
*Suture.*—Nearly smooth, extends from base to apex.
*Ventral surface.*—Nearly smooth, some fruit very slightly lipped.
*Apex.*—Usually rounded, varies from round to slightly retuse.
*Base.*—Varies from rounded to slightly retuse.
*Cavity.*—Rounded to slightly elongated in suture plane. Average depth 5.7 mm. Average diameter 11.9 mm.

Stem:
*Size.*—Medium to large. Average length 14.5 mm. Average diameter 2.1 mm.
*Color.*—Varies from 2.5GY 5/6 to 5GY 5/6.

Flesh:
*Ripens.*—Relatively even, slightly earlier near apex.
*Texture.*—Firm, meaty.
*Fibers.*—Few, small, tender.
*Firmness.*—Firm, comparable to 'Red Beaut' Plum (U.S. Plant Pat. No. 2,539).
*Aroma.*—Slight.
*Amydgalin.*—Undetected.
*Eating quality.*—Very good.
*Flavor.*—Very good, good balance between acid and sugar.
*Juice.*—Moderate, enhances flavor.
*Brix.*—Average 16.3°, varies slightly with amount of fruit per tree and climatic conditions.
*Color.*—Varies from 5Y 8/6 to 5Y 8/8. Pit cavity varies from 2.5Y 7/8 to 5Y 7/8.

Skin:
*Thickness.*—Medium.
*Surface.*—Smooth.
*Bloom.*—Moderate amount, complete coverage.
*Tendency to crack.*—Very slight.
*Color.*—Ground color varies from 5Y 7/8 to 7.5Y 7/8. Partially overspread with 2.5R 2/6 to 5R 3/8, with the degree of red color in direct relationship to fruit exposure to sun. Very small, randomly spaced areas of ground color exposed to give a speckling pattern to red skin areas.
*Tenacity.*—Tenacious to flesh.
*Astringency.*—Undetected.

Stone:
*Type.*—Clingstone.
*Size.*—Medium to large. Average length 23.7 mm. Average width 20.3 mm. Average thickness 8.7 mm.
*Form.*—Ovoid.
*Base.*—Usually flat, varies from flat to rounded.
*Apex.*—Varies from rounded to slight point. Length 0.4 mm.
*Surface.*—Slightly pitted throughout, one shallow groove on each side of suture extending from base to apex.
*Sides.*—Unequal, with one side extending further from suture plane.
*Ridges.*—Several, small, short ridges running from base toward apex.
*Tendency to split.*—None.
*Color.*—Varies from 10YR 6/4 to 10YR 5/6 when dry.

Kernal:
*Form.*—Ovate.
*Taste.*—Bitter.
*Viability.*—Poor viability, embryo only partially developed.
*Size.*—Medium. Average length 14.6 mm. Average width 9.9 mm. Average depth 4.9 mm.
*Skin color.*—Varies from 5YR 6/8 to 5YR 4/8 when dry.

Use: Dessert. Market — local and long distance.

Keeping quality: Good, held firm in cold storage 21 days at 38° to 42° F. without internal breakdown of flesh or appreciable loss of flavor.

Shipping quality: Good, minimal flesh bruising or skin scarring during picking and packing trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described, characterized by its large size, vigorous, upright growth and being a productive and regular bearer of medium to large, yellow flesh, clingstone fruit with very good flavor and eating quality; the fruit is further characterized by maturing in the early season with firm fruit that is relatively uniform in size throughout the tree.

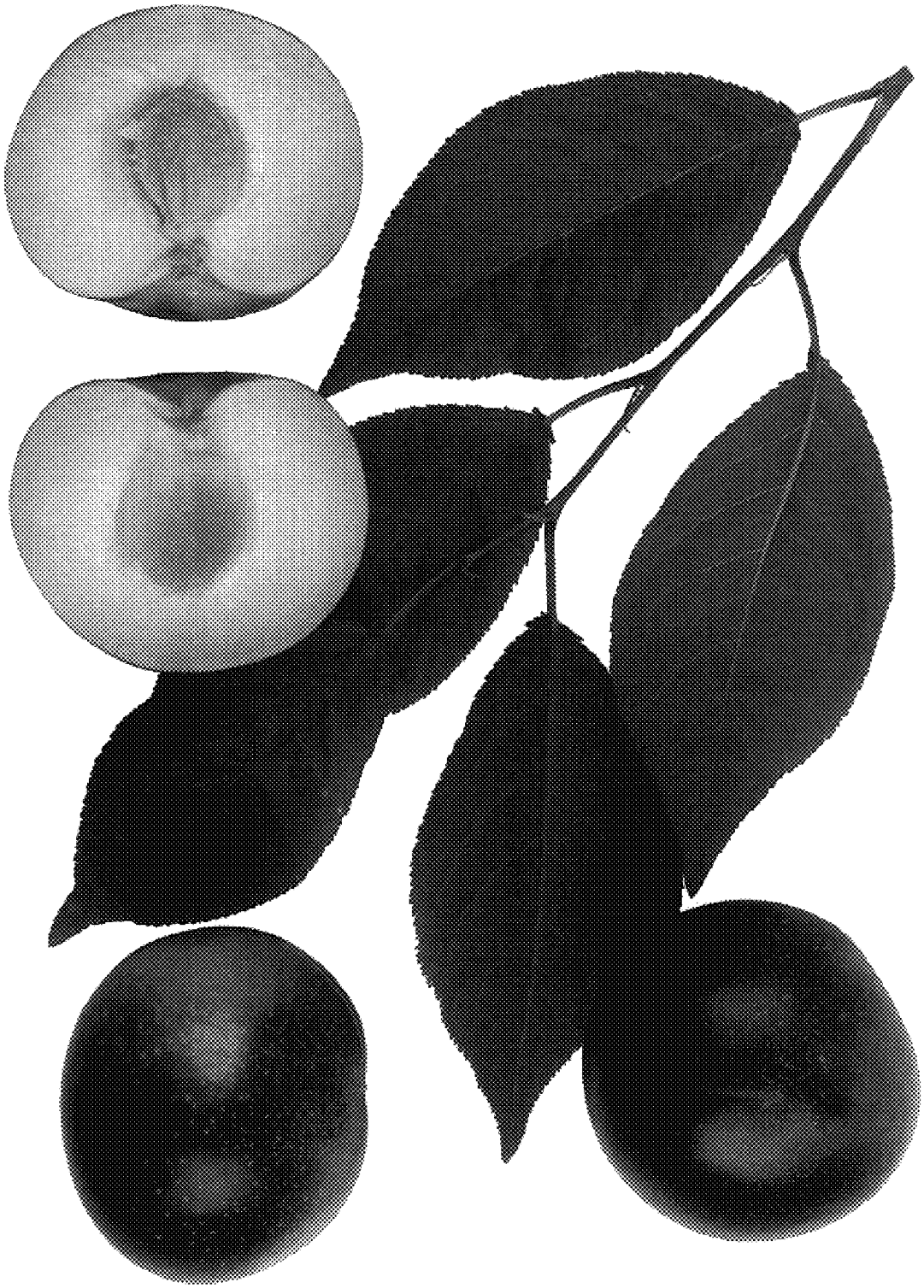

* * * * *